US012779098B2

(12) United States Patent
Fällman et al.

(10) Patent No.: US 12,779,098 B2
(45) Date of Patent: Nov. 3, 2026

(54) DIALYSIS SYSTEM HAVING PATIENT LINE OCCLUSION DETECTION AND INTRAPERITONEAL PRESSURE ESTIMATION

(71) Applicants: Vantive US Healthcare LLC, Deerfield, IL (US); Vantive Health GmbH, Glattpark (Opfikon) (CH)

(72) Inventors: Oskar Erik Frode Styrbjörn Fällman, Lund (SE); Mattias Holmer, Lund (SE); Michael Pettersson, Malmö (SE)

(73) Assignees: Vantive US Healthcare LLC, Deerfield, IL (US); Vantive Health GmbH, Glattpark (Opfikon) (CH)

( * ) Notice: Subject to any disclaimer, the term of this patent is extended or adjusted under 35 U.S.C. 154(b) by 287 days.

(21) Appl. No.: 18/395,819

(22) Filed: Dec. 26, 2023

(65) Prior Publication Data

US 2025/0205402 A1 Jun. 26, 2025

(51) Int. Cl.
*A61M 1/28* (2006.01)
*A61M 1/16* (2006.01)

(52) U.S. Cl.
CPC .......... *A61M 1/281* (2014.02); *A61M 1/1613* (2014.02); *A61M 1/28* (2013.01); *A61M 1/282* (2014.02); *A61M 2205/10* (2013.01); *A61M 2205/125* (2013.01); *A61M 2205/128* (2013.01); *A61M 2205/18* (2013.01); *A61M 2205/3327* (2013.01); *A61M 2205/3331* (2013.01); *A61M 2205/3334* (2013.01); *A61M 2205/3351* (2013.01); *A61M 2205/52* (2013.01); *A61M 2205/7527* (2013.01)

(58) Field of Classification Search
CPC ...... A61M 1/1613; A61M 1/28; A61M 1/281; A61M 1/282; A61M 2205/10; A61M 2205/125; A61M 2205/128; A61M 2205/18; A61M 2205/3327; A61M 2205/3331; A61M 2205/3334; A61M 2205/3351; A61M 2205/52; A61M 2205/7527
See application file for complete search history.

(56) References Cited

U.S. PATENT DOCUMENTS 5,695,473 A * 12/1997 Olsen .................... A61M 5/172 604/153
2023/0137696 A1 * 5/2023 Ericson ................. A61M 1/282 604/29

* cited by examiner

*Primary Examiner* — John Kim
(74) *Attorney, Agent, or Firm* — K&L Gates LLP

(57) ABSTRACT

A peritoneal dialysis ("PD") system includes a PD fluid pump configured to pump PD fluid along a line under negative pressure and to create a negative pressure profile having a maximum negative pressure and a minimum negative pressure; a pressure sensor positioned and arranged to sense the negative pressure profile and to produce an output indicative of the negative pressure profile including a maximum negative pressure output and a minimum negative pressure output; and a control unit configured to analyze the output indicative of the negative pressure profile and to determine that an occlusion in the line has occurred if both the maximum negative pressure output and the minimum negative pressure output change by at or more than a set pressure delta, wherein the set pressure delta is optionally the same pressure delta for the maximum negative pressure output and the minimum negative pressure output.

17 Claims, 8 Drawing Sheets

DIALYSIS SYSTEM HAVING PATIENT LINE OCCLUSION DETECTION AND INTRAPERITONEAL PRESSURE ESTIMATION

TECHNICAL FIELD

The present disclosure relates generally to medical fluid treatments.

BACKGROUND

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. Automated PD machines, however, perform the cycles automatically, typically while the patient sleeps. The PD machines free patients from having to manually perform the treatment cycles and from having to transport supplies during the day. The PD machines connect fluidly to an implanted catheter, to a source or bag of fresh dialysis fluid and to a fluid drain. The PD machines pump fresh dialysis fluid from a dialysis fluid source, through the catheter and into the patient's peritoneal chamber. The PD machines also allow for the dialysis fluid to dwell within the chamber and for the transfer of waste, toxins and excess water to take place. The source may include multiple liters of dialysis fluid including several solution bags.

The PD machines pump used or spent dialysate from the patient's peritoneal cavity, though the catheter, to drain. As with the manual process, several drain, fill and dwell cycles occur during dialysis. A "last fill" may occur at the end of an APD treatment. The last fill fluid may remain in the peritoneal chamber of the patient until the start of the next treatment, or may be manually emptied at some point during the day.

SUMMARY

The present disclosure sets forth an automated peritoneal dialysis ("PD") system and associated methodology, which determine if an occlusion has occurred within a portion of the PD fluid pathway, such as a patient line during a patient drain of the PD treatment. The present disclosure also sets forth an automated peritoneal dialysis ("PD") system and associated methodology, which determine the intraperitoneal pressure of a patient during therapy. The system includes a PD machine or cycler. The PD machine is capable of delivering fresh, heated PD fluid to the patient at, for example, 14 kPa (2.0 psig) or higher. The PD machine is capable of removing used PD fluid or effluent from the patient at, for example, −9 kPa (−1.3 psig) or lower Fresh PD fluid is delivered in one embodiment via a dual lumen patient line to the patient and is first heated to body fluid temperature, e.g., 37° C. The heated PD fluid is then pumped through a fresh PD fluid lumen of the dual lumen patient line to a disposable filter set. The disposable filter set communicates fluidly with the fresh and used PD fluid lumens of the dual lumen patient line, which are heat disinfected and reusable in one embodiment. The disposable filter set includes a sterilizing grade filter membrane that further filters fresh PD fluid. The disposable filter set is provided in one embodiment with one or more hydrophobic filters or vents upstream from the sterilizing grade filter membrane.

A used PD fluid lumen of the dual lumen patient line carries used PD fluid or effluent from the disposable filter set back to the PD machine. The used PD fluid or effluent is pumped along one or more internal line of the PD machine to a flexible, e.g., disposable, drain line, which carries the used PD fluid or effluent to a drain container or house drain. A PD fluid pump of the PD machine is located along one of the internal lines and pumps used PD fluid or effluent under negative pressure to the PD fluid pump and under positive pressure from the PD fluid pump. One or more pressure sensor is located along the internal line (or a line in fluid communication with the internal line) so as to sense the negative pressure of used PD fluid or effluent drawn to the PD fluid pump. Likewise, one or more pressure sensor may be applied to an internal line (or a line in fluid communication with the internal line) extending from the PD fluid pump to a fresh PD fluid lumen of the dual lumen patient line for sensing positive pressure during a patient fill.

In light of the disclosure set forth herein, and without limiting the disclosure in any way, in a first aspect of the present disclosure, which may be combined with any other aspect, or portion thereof, a peritoneal dialysis ("PD") system includes a PD fluid pump configured to pump PD fluid along a line under an upstream pressure and to create an upstream pressure profile having a maximum upstream pressure and a minimum upstream pressure; a pressure sensor positioned and arranged to sense the upstream pressure profile and to produce an output indicative of the upstream pressure profile including a maximum upstream pressure output and a minimum upstream pressure output; and a control unit configured to analyze the output indicative of the upstream pressure profile and to determine that an occlusion in the line has occurred if both the maximum upstream pressure output and the minimum upstream pressure output change by at or more than a set pressure delta, wherein the set pressure delta is optionally the same pressure delta for the maximum upstream pressure output and the minimum upstream pressure output.

In a second aspect of the present disclosure, which may be combined with any other aspect, or portion thereof, the set pressure delta is different for the maximum upstream pressure output and the minimum upstream pressure output.

In a third aspect of the present disclosure, which may be combined with any other aspect, or portion thereof, the set pressure delta is selected to avoid a false occlusion detection in the line and so as to detect a partial occlusion in the line.

In a fourth aspect of the present disclosure, which may be combined with any other aspect, or portion thereof, the upstream pressure profile is a sinusoidal profile.

In a fifth aspect of the present disclosure, which may be combined with any other aspect, or portion thereof, the line under upstream pressure is a flexible patient line and optionally a used PD fluid lumen of a flexible dual lumen patient line.

In a sixth aspect of the present disclosure, which may be combined with any other aspect, or portion thereof, the line under upstream pressure is an internal line of a PD machine of the PD system.

In a seventh aspect of the present disclosure, which may be combined with any other aspect, or portion thereof, the PD fluid pump is located along an internal line in fluid communication with the line under upstream pressure, and wherein the pressure sensor is positioned and arranged along the internal line or a third line in fluid communication with the internal line.

In an eighth aspect of the present disclosure, which may be combined with any other aspect, or portion thereof, the control unit is configured to determine the change by comparing (i) a most recent maximum upstream pressure output to a next most recent maximum upstream pressure output, and (ii) a most recent minimum upstream pressure output to a next most recent minimum upstream pressure output.

In a ninth aspect of the present disclosure, which may be combined with any other aspect, or portion thereof, the control unit is configured to determine the change by comparing (i) a most recent maximum upstream pressure output to an average maximum upstream pressure output including a next most recent maximum upstream pressure output, and (ii) a most recent minimum upstream pressure output to an average minimum upstream pressure output including a next most recent minimum upstream pressure output.

In a tenth aspect of the present disclosure, which may be combined with any other aspect, or portion thereof, at least one of the average maximum upstream pressure output or the average minimum upstream pressure output is a rolling average.

In an eleventh aspect of the present disclosure, which may be combined with any other aspect, or portion thereof, the control unit is configured to determine the change by comparing (i) an average maximum upstream pressure output including a most recent maximum upstream pressure output and at least one other maximum upstream pressure output to (a) a maximum upstream pressure output just prior to the at least one other maximum upstream pressure output or (b) a second average maximum upstream pressure output including the just prior maximum upstream pressure output, and (ii) an average minimum upstream pressure output including a most recent minimum upstream pressure output and at least one other minimum upstream pressure output to (a) a minimum upstream pressure output just prior to the at least one other minimum upstream pressure output or (b) a second average minimum upstream pressure output including the just prior minimum upstream pressure output.

In a twelfth aspect of the present disclosure, which may be combined with any other aspect, or portion thereof, the control unit is configured such that upon determining that an occlusion in the line has occurred, at least one of (i) the PD fluid pump is stopped or (ii) an alarm is sounded and/or displayed.

In a thirteenth aspect of the present disclosure, which may be combined with any other aspect, or portion thereof, the upstream pressure is a negative pressure.

In a fourteenth aspect of the present disclosure, which may be combined with any other aspect, or portion thereof, a peritoneal dialysis ("PD") system includes a PD fluid pump configured to pump PD fluid along a line under pressure and to create a pressure profile having a maximum pressure and a minimum pressure; a pressure sensor positioned and arranged to sense the pressure profile and to produce an output indicative of the pressure profile including a maximum pressure output and a minimum pressure output; and a control unit configured to analyze the output indicative of the pressure profile and to determine that an occlusion in the line has occurred if both the maximum pressure output and the minimum pressure output change by at or more than a set pressure delta, wherein the set pressure delta is optionally the same pressure delta for the maximum pressure output and the minimum pressure output.

In a fifteenth aspect of the present disclosure, which may be combined with any other aspect, or portion thereof, the PD fluid pump is configured to pump PD fluid along the line under negative pressure, and wherein the maximum pressure output is a maximum negative pressure output and the minimum pressure output is a minimum negative pressure output.

In a sixteenth aspect of the present disclosure, which may be combined with any other aspect, or portion thereof, the line is (i) a patient line, optionally a used PD fluid lumen of a dual lumen patient line or (ii) a PD fluid supply line.

In a seventeenth aspect of the present disclosure, which may be combined with any other aspect, or portion thereof, the PD fluid pump is configured to pump PD fluid along the line under positive pressure, and wherein the maximum pressure output is a maximum positive pressure output and the minimum pressure output is a minimum positive pressure output.

In an eighteenth aspect of the present disclosure, which may be combined with any other aspect, or portion thereof, a peritoneal dialysis ("PD") method includes during a non-treatment mode, determining a pressure profile created by a PD fluid pump configured to pump PD fluid along a line under pressure, wherein the pressure profile includes a maximum pressure and a minimum pressure; positioning a pressure sensor so as to sense the pressure PD fluid profile, the pressure sensor producing an output indicative of the pressure profile including a maximum non-treatment pressure output and a minimum non-treatment pressure output; and analyzing an output indicative of a pressure profile occurring during treatment and determining that an occlusion in the line has occurred if both (i) a difference between a maximum treatment pressure output and the maximum non-treatment pressure output is at or more than a set pressure delta and (ii) a difference between a minimum treatment pressure output and the minimum non-treatment pressure output is at or more than the set pressure delta, wherein the set pressure delta is optionally the same pressure delta for the maximum pressure difference and the minimum pressure difference.

In a nineteenth aspect of the present disclosure, which may be combined with any other aspect, or portion thereof, peritoneal dialysis ("PD") system includes a housing, a PD fluid pump housed by the housing, a dual lumen patient line extending from the housing, the dual lumen patient line including a fresh PD fluid lumen and a used PD fluid lumen. a filter set in fluid communication with the fresh PD fluid lumen, one or more vents positioned upstream from the filter set, a first pressure sensor in fluid contact with the fresh PD fluid lumen; and a control unit. The control unit is configured to (i) determine a hydrostatic pressure by receiving a first pressure value from the first pressure sensor during a patient drain.

In a twentieth aspect of the present disclosure, which may be combined with any other aspect, or portion thereof, the PD system includes a second pressure sensor in fluid contact with the used PD fluid lumen. The controller is further configured to (ii) determine when a flow rate of fluid through the fresh PD lumen and the used PD lumen is zero; (iii) receive a second pressure value from the second pressure sensor when the flow rate is zero; and (iv) estimate an intra peritoneal pressure of a patient using the second pressure value and the hydrostatic pressure.

In a twenty-first aspect of the present disclosure, which may be combined with any other aspect, or portion thereof, estimating the intra peritoneal pressure of the patient includes subtracting hydrostatic pressure from the second pressure value.

In a twenty-second aspect of the present disclosure, which may be combined with any other aspect, or portion thereof, the controller is configured to repeat (i) to (iv) during each treatment of the patient.

In a twenty-third aspect of the present disclosure, which may be combined with any other aspect, or portion thereof, the controller is configured to: (i) store the intra peritoneal pressure values for each treatment; (ii) determine a variation of intra peritoneal pressure values between each treatment; and (iii) issue an alarm if the variation is above a predetermined threshold.

In a twenty-fourth aspect of the present disclosure, which may be combined with any other aspect, or portion thereof, the filter set includes a hydrophilic membrane In a twenty-fifth aspect of the present disclosure, which may be combined with any other aspect, or portion thereof, the vent includes a hydrophobic membrane In a twenty-sixth aspect of the present disclosure, which may be combined with any other aspect, or portion thereof, a peritoneal dialysis ("PD") system includes a housing, a PD fluid pump housed by the housing, a dual lumen patient line extending from the housing, the dual lumen patient line including a fresh PD fluid lumen and a used PD fluid lumen, a valve positioned on the fresh PD fluid lumen, wherein the valve is configured to close during a patient drain, a filter set in fluid communication with the fresh PD fluid lumen, the filter set comprising a hydrophilic membrane, and one or more vents positioned upstream from the filter set, the one or more vents comprising a hydrophobic membrane. The pump is configured to draw fluid through the used PD fluid lumen during the patient drain causing air to become trapped between the hydrophobic membrane and the hydrophilic membrane.

In a twenty-seventh aspect of the present disclosure, which may be combined with any other aspect, or portion thereof, the PD system includes a first pressure sensor in fluid contact with the fresh PD fluid lumen; and a control unit configured to: (i) determine a hydrostatic pressure by receiving a first pressure value from the first pressure sensor during the patient drain.

In a twenty-eighth aspect of the present disclosure, which may be combined with any other aspect, or portion thereof, the PD system includes a second pressure sensor in fluid contact with the used PD fluid lumen. The controller is further configured to determine when a flow rate of fluid through the fresh PD lumen and the used PD lumen is zero; receive a second pressure value from the second pressure sensor when the flow rate is zero; and (v) estimate an intra peritoneal pressure of a patient using the second pressure value and the hydrostatic pressure.

In a twenty-ninth aspect of the present disclosure, which may be combined with any other aspect, or portion thereof, any of the features, functionality and alternatives described in connection with any one or more of FIGS. 1 to 8 may be combined with any of the features, functionality and alternatives described in connection with any other of FIGS. 1 to 8.

In light of the above aspects and present disclosure set forth herein, it is an advantage of the present disclosure to provide a peritoneal dialysis occlusion detection system and associated methodology having an improved response time.

It is another advantage of the present disclosure to provide a peritoneal dialysis occlusion detection system and associated methodology that is repeatable and reliable.

It is a further advantage of the present disclosure to provide a peritoneal dialysis occlusion detection system and associated methodology that uses existing equipment that is used for other purposes.

Moreover, it is an advantage of the present disclosure to provide a peritoneal dialysis occlusion detection system and associated methodology that uses a larger portion of a pressure sensor output profile and has an increased response time to an occlusion, enabling the patient drain to occur at a higher flowrate and resulting in an improved peritoneal dialysis treatment.

It is yet another advantage of the present disclosure to provide a peritoneal dialysis system that can determine the hydrostatic pressure associated with a pressure sensor inside the PD system to determine intra peritoneal pressure.

Moreover, it is an advantage of the present disclosure to provide a PD system determines a change in intra peritoneal pressure over time to determine problems in the system.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

System Generally

Figure 1:
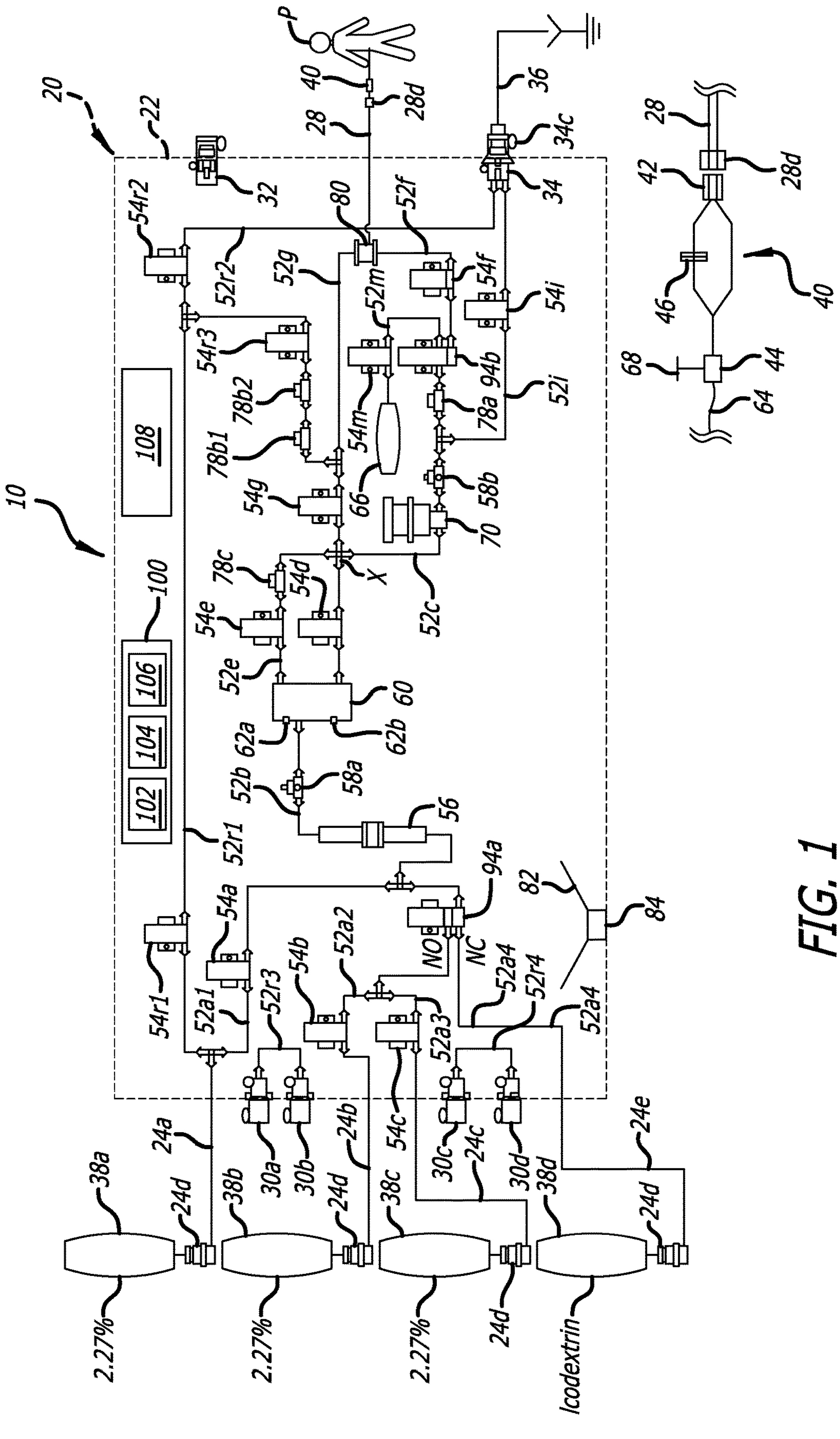
FIG. 1 is a fluid flow schematic of one embodiment for a medical fluid, e.g., PD fluid, system having the patient line occlusion detection structure and methodology of the present disclosure.

Referring now to the drawings and in particular to FIG. 1, the patient line occlusion detection structure and methodology of the present disclosure is illustrated via peritoneal dialysis ("PD") system 10. System 10 includes a PD machine or cycler 20 and a control unit 100 having one or more processor 102, one or more memory 104, video controller 106 and user interface 108. User interface 108 may alternatively or additionally be a remote user interface, e.g., via a tablet or smartphone. Control unit 100 may also include a transceiver and a wired or wireless connection to a network (not illustrated), e.g., the internet, for sending treatment data to and receiving prescription instructions/changes from a doctor's or clinician's server interfacing with a doctor's or clinician's computer. Control unit 100 in an embodiment controls all electrical fluid flow and heating components of system 10 and receives outputs from all sensors of system 10. System 10 in the illustrated embodiment includes durable and reusable components that contact fresh and used PD fluid, which necessitates that PD machine or cycler 20 be disinfected between treatments, e.g., via heat disinfection.

System 10 in FIG. 1 may include an inline resistive heater 56, reusable supply lines or tubes **52*a*1 to 52*a*4 and 52*b*, air trap 60 operating with respective upper and lower level sensors 62*a* and 62*b*, air trap valve 54*d*, vent valve 54*e* located along vent line 52*e*, reusable line or tubing 52*c*, PD fluid pump 70, temperature sensors 58*a* and 58*b*, reusable line or tubing 52*d*, pressure sensors 78*a*, 78*b*1, 78*b*2 and 78*c*, reusable patient tubing or lines 52*f* and 52*g* having respective valves 54*f* and 54*g*, dual lumen reusable patient line 28, a hose reel 80 for retracting patient line 28, reusable drain tubing or line 52*i* extending to drain line connector 34 and having a drain line valve 54*i*, and reusable recirculation disinfection tubing or lines 52*r*1 and 52*r*2 operating with respective disinfection valves 54*r*1 and 54*r*2. A third recirculation or disinfection tubing or line 52*r*3 extends between lines 52*g* and 52*r*1. A fourth recirculation or disinfection tubing or line 52*r*4 extends between disinfection connectors 30*a* and 30*b* for use during disinfection. A fifth recirculation or disinfection tubing or line 52*r*5 extends between disinfection connectors 30*c* and 30*d*** for use during disinfection.

System 10 may also include PD fluid containers or bags **38*a* to 38*c* (e.g., holding the same or different formulations of PD fluid), which connect to distal ends 24*d* of reusable PD fluid lines 24*a* to 24*c*, respectively. System 10*d* further includes a fourth PD fluid container or bag 38*d* that connects to a distal end 24*d* of reusable PD fluid line 24*e*. Fourth PD fluid container or bag 38*d* may hold the same or different type (e.g., icodextrin) of PD fluid than provided in PD fluid containers or bags 38*a* to 38*c*. Reusable PD fluid lines 24*a* to 24*c* and 24*e* extend in one embodiment through apertures (not illustrated) defined or provided by housing 22 of cycler 20**.

System 10 in the illustrated embodiment includes four disinfection connectors **30*a* to 30*d* for connecting to distal ends 24*d* of reusable PD fluid lines 24*a* to 24*c* and 24*e*, respectively, during disinfection. System 10 also provides a patient line connector 32 that includes an internal lumen, e.g., a U-shaped lumen, which for disinfection directs fresh or used dialysis fluid from one PD fluid lumen of a connected distal end 28***d* of dual lumen reusable patient line 28 into the other PD fluid lumen. Reusable supply tubing or lines 52*a*1 to 52*a*4 communicate with reusable supply lines 24*a* to 24*c* and 24*e*, respectively. Reusable supply tubing or lines 52*a*1 to 52*a*3 operate with valves 54*a* to 54*c*, respectively, to allow PD fluid from a desired PD fluid container or bag 38*a* to 38*c* to be pulled into cycler 20. Three-way valve 94*a* in the illustrated example allows for control unit 100 to select between (i) 2.27% (or other) glucose dialysis fluid from container or bag 38*b* or 38*c* and (ii) icodextrin from container or bag 38*d*. In the illustrated embodiment, icodextrin from container or bag 38*d* is connected to the normally closed port of three-way valve 94*a*.

System 10 is constructed in one embodiment such that drain line 52*i* during a patient fill is fluidly connected downstream from PD fluid pump 70. In this manner, if drain valve 54*i* fails or somehow leaks during the patient fill of patient P, fresh PD fluid is pushed down disposable drain line 36 instead of used PD fluid potentially being pulled into pump 70. Disposable drain line 36 is in one embodiment removed for disinfection, wherein drain line connector 34 is capped via a cap 34*c* to form a closed disinfection loop. PD fluid pump 70 may be an inherently accurate pump, such as a piston pump, or less accurate pump, such as a gear pump that operates in cooperation with a flowmeter (not illustrated) to control fresh and used PD fluid flowrate and volume.

System 10 may further include a leak detection pan 82 located at the bottom of housing 22 of cycler 20 and a corresponding leak detection sensor 84 outputting to control unit 100. In the illustrated example, system 10 is provided with an additional pressure sensor 78*c* located upstream of PD fluid pump 70, which allows for the measurement of the suction pressure of pump 70 to help control unit 100 more accurately determine pump volume. Additional pressure sensor 78*c* in the illustrated embodiment is located along vent line 52*e*, which may be filled with air or a mixture of air and PD fluid, but which should nevertheless be at the same negative pressure as PD fluid located within PD fluid line 52*c*.

System 10 in the example of FIG. 1 includes redundant pressure sensors 78*b*1 and 78*b*2, the output of one of which is used for pump control, as discussed herein, while the output of the other pressure sensor is a safety or watchdog output to make sure the control pressure sensor is reading accurately. Pressure sensors 78*b*1 and 78*b*2 are located along recirculation line 52*r*3 including a third recirculation valve 54*r*3. In still a further example, system 10 may employ one or more cross, marked via an X in FIG. 1, which may (i) reduce the overall amount and volume of the internal, reusable tubing, (ii) reduce the number of valves needed, and (iii) allow the portion of the fluid circuitry shared by both fresh and used PD fluid to be minimized.

System 10 in the example of FIG. 1 further includes a source of acid, such as a citric acid container or bag 66. Citric acid container or bag 66 is in selective fluid communication with second three-way valve 94*b* via a citric acid valve 54*m* located along a citric acid line 52*m*. Citric acid line 52*m* is connected in one embodiment to the normally closed port of second three-way valve 94*b*, so as to provide redundant valves between citric acid container or bag 66 and the PD fluid circuit during treatment. The redundant valves ensure that no citric (or other) acid reaches the treatment fluid lines during treatment. Citric (or other) acid is instead used during disinfection.

Control unit 100 in an embodiment uses feedback from any one or more of pressure sensors 78*a* to 78*c* to enable PD machine 20 to deliver fresh, heated PD fluid to the patient at, for example, 14 kPa (2.0 psig) or higher. The pressure feedback is used to enable PD machine 20 to remove used PD fluid or effluent from the patient at, for example, −9 kPa (−1.3 psig) or higher. The pressure feedback may be used in a proportional, integral, derivative ("PID") pressure routine for pumping fresh and used PD fluid at a desired positive or negative pressure.

Inline resistive heater 56 under control of control unit 100 is capable of heating fresh PD fluid to body temperature, e.g., 37° C., for delivery to patient P at a desired flowrate. Control unit 100 in an embodiment uses feedback from temperature sensor 58*a* in a PID temperature routine for pumping fresh PD fluid to patient P at a desired temperature.

FIG. 1 also illustrates that system 10 includes and uses a disposable filter set 40, which communicates fluidly with the fresh and used PD fluid lumens of dual lumen reusable patient line 28. Disposable filter set 40 includes a disposable connector 42 that connects to a distal end 28*d* of reusable patient line 28. Disposable filter set 40 also includes a connector 44 that connects to the patient's transfer set. Disposable filter set 40 further includes a sterilizing grade filter membrane 46 that further filters fresh PD fluid. Disposable filter set 40 is provided in one embodiment as a last chance filter for PD machine 20, which has been heat disinfected between treatments. Any pathogens that remain after disinfection, albeit unlikely, are filtered from the PD fluid via the sterilizing grade filter membrane 46 of disposable filter set 40.

Occlusion Detection

Figure 2:
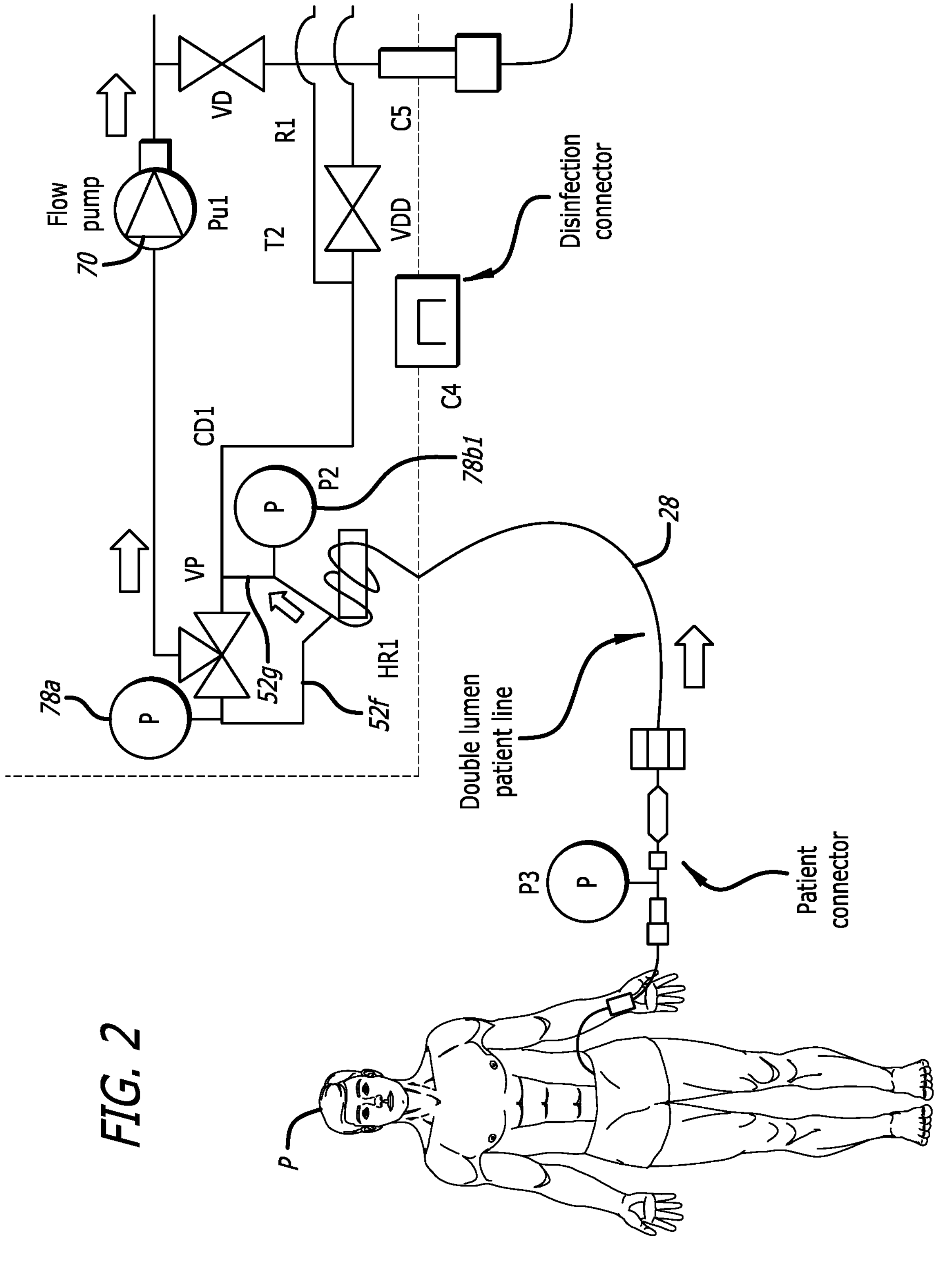
FIG. 2 is a partial fluid flow schematic of one embodiment for a medical fluid system of the present disclosure.
Figure 3:
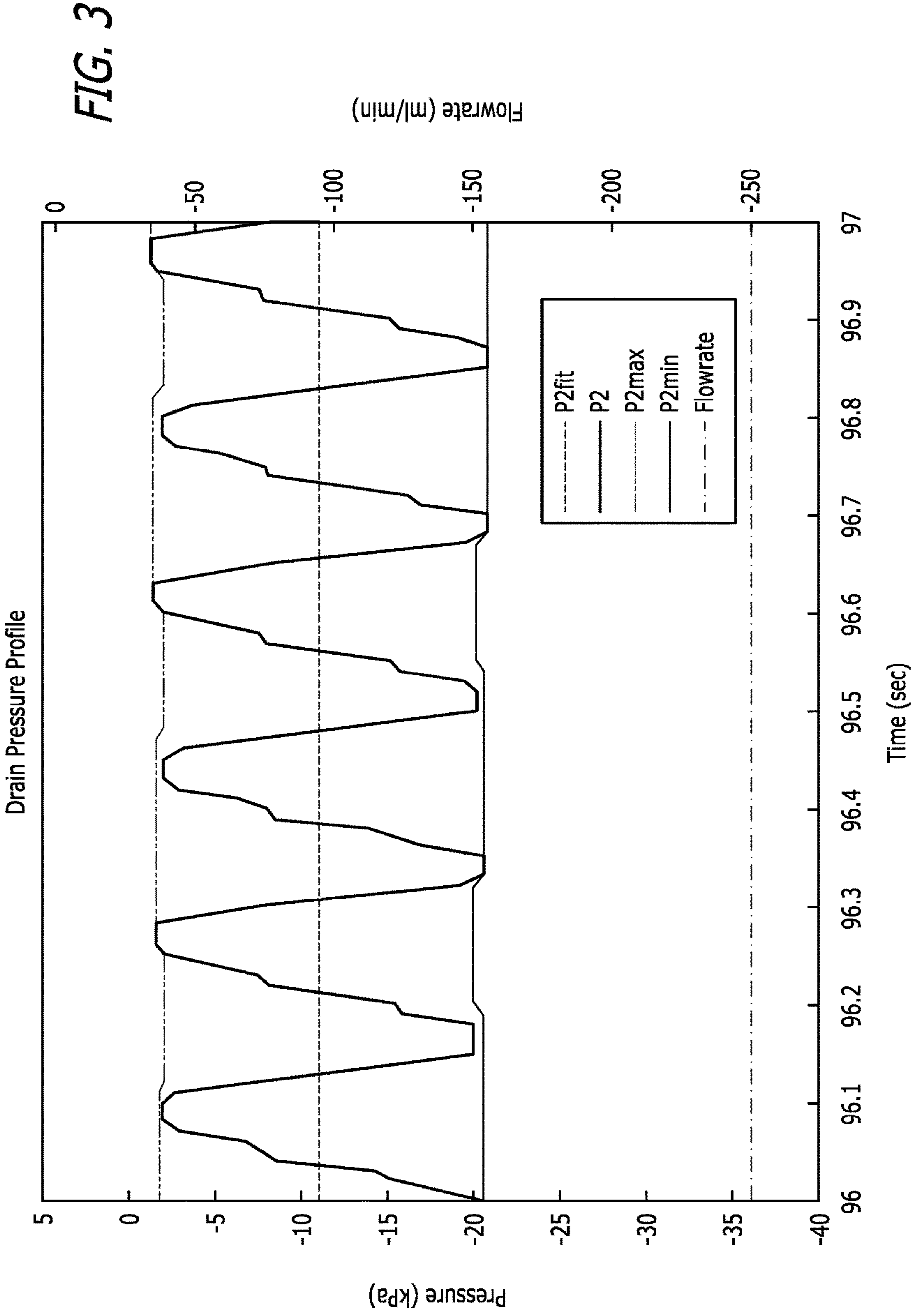
FIG. 3 is a plot of negative pressure over multiple PD fluid pump strokes, a maximum pressure plot showing maximum peak negative pressure values, a minimum pressure plot showing minimum peak negative pressure values, a filtered negative pressure plot, and a plot of a corresponding patient drain PD flowrate.
Figure 4:
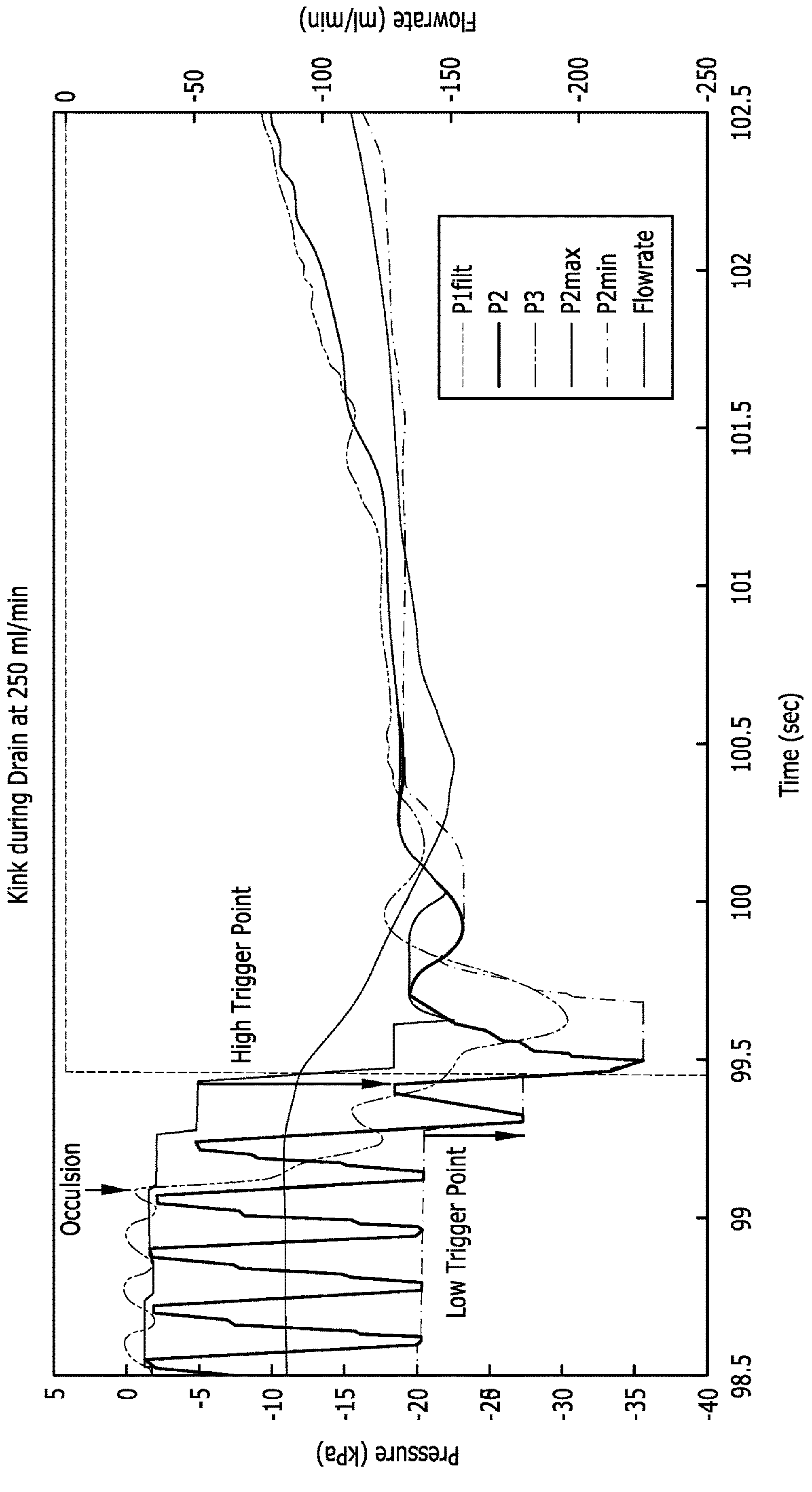
FIG. 4 shows the plots of FIG. 3 along with a plot from a test pressure sensor placed at an access point to the patient, wherein each of the plots illustrate a characteristic response to a line or tube occlusion.

Referring to FIG. 1, an embodiment for the occlusion detection is applied to used PD fluid lumen of dual lumen patient line 28, which carries used PD fluid or effluent from disposable filter set 40 back to PD machine 20. The used PD fluid or effluent is pumped along internal lines 52*g*, 52*c* and 52*i* of PD machine 20 to a flexible, e.g., disposable, drain line 36, which carries the used PD fluid or effluent to a drain container or house drain. PD fluid pump 70 is located along internal line 52*c* and pumps the used PD fluid or effluent under negative pressure to the PD fluid pump and under positive pressure from the PD fluid pump. FIG. 2 illustrates a partial schematic of the drain fluid flow path. One or more pressure sensor indicated as P2 in FIGS. 3 and 4 is located along internal used PD fluid line 52*g* (or an internal line 52*e*, 52*r*3 in fluid communication with the used PD fluid line 52*g*) so as to sense the negative pressure of used PD fluid or effluent drawn into PD fluid pump 70. In FIG. 1, pressure sensor P2 may be any one or more of pressure sensor 78*c* located long line 52*e* or pressure sensors 78*b*1 and/or 78*b*2 located line 52*r*3.

Likewise, one or more pressure sensor 78*a* may be located along an internal fresh PD fluid line 52*f* (or a line in fluid communication with the fresh PD fluid line 52*f*) extending from PD fluid pump 70 to a fresh PD fluid lumen of dual lumen patient line 28 for sensing positive pressure during a patient fill. The output of one or more pressure sensor P2 (sensor 78*b*1, 78*b*2 and/or 78*c*) is/are used by control unit 100 to detect an occlusion (i) in the used PD fluid lumen of flexible dual lumen patient line 28 or (ii) in any of flexible, reusable PD fluid lines 24*a* to 24*c* and 24*e*. The output of pressure sensor 78*a* is used by control unit 100 in one embodiment to detect an occlusion in the used PD fluid lumen of flexible dual lumen patient line 28.

FIG. 1 further illustrates that an additional pressure measurement P3 may be taken at the PD fluid access to patient P. An additional pressure sensor may be located at the patient's transfer set (leading to an indwelling PD catheter)

for taking pressure measurement P3. The additional pressure sensor and pressure measurement P3 are not provided with system 10 in one embodiment, however, pressure measurement P3 does provide a useful comparison to the pressure plots of FIG. 4.

PD fluid pump 70 may be any type of fluid pump, such as a piston pump or peristaltic pump. FIG. 3 illustrates that for each type of PD fluid pump 70, the upstream (e.g., negative) pressure profile of pressure sensor P2 (sensor **78*b*1, 78*b*2 and/or 78*c*) measured by control unit 100** under normal circumstances (no occlusion) is a sinusoidal profile in which a highest negative pressure (e.g., −2 kPa (−0.3 psig) is reached at the beginning of a negative pressure portion of a pump stroke, while a lowest negative pressure (e.g., −20 kPa (−3 psig)) is reached at the end of the negative pressure portion of a pump stroke. As used herein when describing negative pressures, "high" means closer to zero in the negative direction, while "low" means further from zero in the negative direction. Thus, for example, −20 kPa (−3 psig) is a lower negative pressure than −2 kPa (−0.3 psig).

FIG. 3 also illustrates a plot (P2filt) of the output of pressure sensor P2 (sensor **78*b*1, 78*b*2 and/or 78*c*) that has been filtered by control unit 100, e.g., via a high pass filter, low pass filter, or combination band pass filter. The filtered output profile (P2filt) shows, under normal circumstances (no occlusion), a steady negative pressure of about −11 kPa (−1.6 psig). FIG. 3 also illustrates plots and that essentially extend from maximum peak to maximum peak (P2max) and from minimum peak to minimum peak (P2 min). Peak output plots P2max and P2 min also show, under normal circumstances (no occlusion), a steady negative pressure of about −2 kPa (−0.3 psig) and −20 kPa (−3 psig), respectively. FIG. 3 further illustrates that a steady drain flowrate of about 250 milliliters (ml) per minute from patient P into the used PD fluid lumen of dual lumen patient line 28** is generated under normal circumstances (no occlusion).

In system 10, one or more processor 102 and one or more memory 104 of control unit 100 are programmed to analyze or apply one or more algorithm to the upstream (e.g., negative) pressure output of pressure sensor P2 (sensor **78*b*1, 78*b*2 and/or 78*c*) during a patient drain to attempt to detect an occlusion in the used fluid lumen of dual lumen patient line 28. The analysis or algorithm as programmed into control unit 100 in an embodiment analyzes the maximum and minimum peaks in the sinusoidal pressure sensor output profile to determine the presence of an occlusion in the used PD fluid lumen of dual lumen patient line 28**.

In one embodiment, the analysis or algorithm of control unit 100 looks to see if both the maximum and minimum peaks in the sinusoidal pressure sensor output profile decrease by more than a threshold pressure change or delta value. If so, control unit 100 determines that an occlusion has occurred, causes PD fluid pump 70 to stop pumping, and may optionally cause an audio, visual or audiovisual alarm to be provided at user interface 108 instructing the patient or caregiver to look for a source of the occlusion. The threshold delta values, e.g., 5 kPa (0.73 psig) or 7 kPa (1.02 psig), may be different for (i) the upper and lower (high/low or maximum/minimum) pressure peaks, and (ii) different types of PD fluid flows, e.g., be different for a patient drain through the used PD fluid lumen of patient line 28, versus a patient fill through the fresh PD fluid lumen of patient line 28, and versus a PD fluid draw through a supply line **24*a* to 24*c*, 24*e* extending to a PD fluid container or bag 38*a* to 38*d*. The present analysis or algorithms may be used for any type of PD fluid that flows through a line or tube that may experience an occlusion, especially along flexible PD fluid lines, such as patient line 28 or PD fluid lines 24*a* to 24*c* and 24*e***. The threshold delta values in an embodiment are selected to be large enough to prevent false occlusion detections but on the other hand small enough to detect partial occlusions (used PD fluid lumen only partially kinked) in addition to full occlusions.

FIG. 4 illustrates an example in which an occlusion occurs along the used PD fluid lumen of dual lumen patient line 28. FIG. 4 includes each of the plots described in connection with FIG. 3, including P2filt, P2, P2max, P2 min and the resulting flowrate. Between time 98.5 seconds and about 99.1 seconds, P2, P2filt, P2max, P2 min and the flowrate under normal circumstances (no occlusion) output as shown in FIG. 3. FIG. 4 also shows an output from pressure measurement P3 taken at patient P discussed above. Pressure measurement P3 shows that the negative pressure peaks are dampened at patient P, such that the patient does not see the larger peak to peak pressure swings as recorded at pressure sensor P2 (sensor **78*b*1, 78*b*2 and/or 78*c*). Pressure measurement P3 is not recorded at PD machine 20 in one embodiment but is provided to show pressures at the patient. Moreover, in one embodiment, control unit 100 of system 10 receives and analyzes only the pressure profile of pressure sensor P2 (sensor 78*b*1, 78*b*2 and/or 78*c*). That is, pressure profiles P2filt, P2max and P2 min are not needed to perform the occlusion detection of system 10**, but may be provided if desired, e.g., for diagnostic and performance evaluation purposes.

FIG. 4 illustrates that slightly after 99.1 seconds, an occlusion occurs in the used PD fluid lumen of dual lumen patient line 28. The occlusion could be the result of patient P crimping the used PD fluid lumen, patient line 28 being twisted, or perhaps an occlusion or flow stoppage occurring within the peritoneal cavity of patient P. Upon the occlusion occurring at 99.1 seconds, the upper pressure peak of P2 decreases from about −2 kPa (−0.3 psig) to −5 kPa (−0.73 psig), and then from −5 kPa (−0.73 psig) to −18.5 kPa (−2.70 psig). Upon the occlusion occurring at 99.1 seconds, the lower pressure peak of P2 decreases from about −20 kPa (−3 psig) to −27 kPa (−3.9 psig). The decrease in the upper pressure peaks (upper pressure peak delta) meets or exceeds a high trigger point stored in control unit 100. The decrease in the lower pressure peaks (lower pressure peak delta) meets or exceeds a low trigger point stored in control unit 100. Control unit 100 is programmed in one embodiment that when both the high and low trigger points are met or exceeded (could be programmed either way to require just being met or having to be exceeded), control unit 100 determines that an occlusion has occurred, causes PD fluid pump 70 to stop pumping, and may optionally cause an audio, visual or audiovisual alarm to be provided at user interface 108, e.g., instructing the patient or caregiver to look for a source of the occlusion.

Upon the occurrence of the occlusion in FIG. 4, the pressure profiles of P2filt, P2max, P2 min and pressure measurement P3 likewise show a pressure decrease. The corresponding used PD fluid or effluent flowrate at about 99.45 seconds shows a sharp decrease to zero ml/min, indicating a full occlusion of the used PD fluid lumen of dual lumen patient line 28. It should be appreciated that in one embodiment, if only one of the high or low trigger points is met or exceeded, control unit 100 does not cause PD fluid pump 70 to stop pumping and does not cause an alarm to be sounded or displayed. Here, however, control unit 100 may be programmed to look to see if the one high or low trigger point that is met or exceeded becomes corrected, so that the pressure plots again appear to be under normal circumstances as in FIG. 3 and the beginning of FIG. 4. If after a certain amount of time or a certain number of pressure oscillations, e.g., one to ten seconds or five to twenty oscillations, the one high or low trigger point that is met or exceeded does not become corrected, then control unit 100 determines that some anomaly or event has occurred, causes PD fluid pump 70 to stop pumping, and may optionally cause an audio, visual or audiovisual alarm to be provided at user interface 108, e.g., instructing the patient or caregiver to look check that all lines, especially, dual lumen patient line 28, are clear.

As discussed above, properly selecting the threshold delta values for the high and low trigger point comparisons is important to prevent false occlusion detections but to also be able to detect partial occlusions. Another important determination is the high and low pressure peaks to which the threshold delta values are applied. Depending on the type of pump for PD fluid pump 70, the pump output including suction and delivery pressures may vary over time. If PD fluid pump 70 is a peristaltic pump, for example, the pump tubing actuated by the peristaltic pump rollers may wear and/or soften over time such that the corresponding pumping output changes, typically degrading.

Also, suction and delivery pressures will vary greatly due to patient head height (relative to PD machine 20) regardless of the type of pump for PD fluid pump 70. Patient head height can vary during treatment, e.g., if the patient sits up from a sleeping position, and can vary from treatment to treatment depending on the location of PD machine 20 and the patient, e.g., sleeping on a couch versus a bed. Patient head height offsets the pulsation of the pressure profile, e.g., offsets the midline pressure axis (see, e.g., FIG. 3 at P2filt). The head height offset may even result in the maximum and minimum values of the pressure profile both having a positive value even when taken upstream of PD fluid pump 70 during a patient drain.

Control unit 100 of system 10 is in one embodiment programmed to compare a most recently sensed set of maximum and minimum (high and low) pressure sensor output peaks to the previously sensed set of maximum and minimum pressure sensor output peaks. Here, if (i) a most recently sensed maximum peak has decreased by at or more than the set pressure delta and (ii) a most recently sensed minimum peak has decreased by at or more than the set pressure delta, then control unit 100 determines that a line occlusion has occurred and takes appropriate action as discussed herein. In FIG. 4, the occlusion occurs at around 99.1 seconds. In this example, the high peak beginning at about 99.4 seconds compared by control unit 100 to the high peak beginning at about 99.25 seconds meets or exceeds the set delta pressure of, e.g., 5 kPa (0.73 psig) and thus sets off the high trigger point. In the same example, the low peak beginning at about 99.3 seconds compared by control unit 100 to the low peak beginning at about 99.15 seconds also meets or exceeds the set delta pressure of, e.g., 5 kPa (0.73 psig) and thus sets off the low trigger point. Because both the high and low trigger points are attained, control unit 100 system determines that an occlusion has occurred, causes PD fluid pump 70 to stop pumping, and may optionally cause an audio, visual or audiovisual alarm to be provided at user interface 108 instructing the patient or caregiver to look for a source of the occlusion.

In an alternative embodiment, control unit 100 again uses the most recently sensed set of maximum and minimum pressure sensor output peaks but instead compares those peaks to an average of multiple sets of prior maximum and minimum pressure sensor output peaks, e.g., a ten set rolling average. So in the above example for FIG. 4, the high peak beginning at about 99.4 seconds is compared by control unit 100 instead to an average of a previous number, e.g., rolling ten high peaks, to determine if the difference meets or exceeds the set high point delta pressure. In the same example, the low peak beginning at about 99.3 seconds is compared by control unit 100 instead to an average of a previous number, e.g., rolling ten low peaks, to determine if the difference meets or exceeds the set low point delta pressure (may be the same or different than the set high point delta pressure).

In a further alternative embodiment, control unit 100 instead compares an average of a number, e.g., two to five, of the most recent sets of maximum and minimum pressure sensor output peaks to (i) the next most recent set of maximum and minimum pressure sensor output peaks or (ii) an average of multiple next most recent sets of maximum and minimum pressure sensor output peaks. So in the above example for FIG. 4, an average of the high peak beginning at about 99.4 seconds formed with one or more prior high peak is compared by control unit 100 instead to (i) the next previous high peak or (ii) an average of a number of the next previous high peaks, to determine if the difference meets or exceeds the set high point delta pressure. In the same example, an average of the low peak beginning at about 99.3 seconds formed with one or more prior low peak is compared by control unit 100 instead to (i) the next previous low peak or (ii) an average of a number of the next previous low peaks, to determine if the difference meets or exceeds the set low point delta pressure (may be the same or different than the set low point delta pressure).

In any of the above embodiments, if both the high and low pressure sensor output differences are at or greater than the corresponding defined or set threshold pressure sensor output deltas, control unit 100 determines that a line occlusion has occurred and takes appropriate action as discussed herein.

System 10 is expressly not limited to occlusion detection during a patient drain. The plots of FIG. 4 could instead be an upstream (e.g., negative) pressure analysis where PD fluid pump 70 is pulling fresh PD fluid from one of the PD fluid containers or bags 38*a* to 38*d* through a corresponding PD fluid line 24*a* to 24*c* or 24*e*, respectively. Here, control unit 100 is looking for an occlusion in the flexible PD fluid line 24*a* to 24*c* or 24*e*. The output values for pressure sensor P2 (sensor 78*b*1, 78*b*2 and/or 78*c*) may look different than as shown in FIG. 4. The threshold pressure delta values may also be different. But the analysis and each of the alternative embodiments discussed above for occlusion detection during a patient drain are equally applicable to determining an occlusion in flexible PD fluid lines 24*a* to 24*c* and 24*e*.

Plots similar to those of FIG. 4 but where the high and low pressure peaks are downstream (e.g., positive) peaks may be used to detect an occlusion in the fresh PD lumen of dual lumen patient line 28 during a patient fill. Again, the output values for, here, pressure sensor 78*a* may have different magnitudes and frequencies than as shown in FIG. 4. The threshold pressure delta values may also be different. But the analysis and each of the alternative embodiments discussed above for occlusion detection during a patient drain are equally applicable to determining an occlusion in the fresh PD lumen of dual lumen patient line 28 during a patient fill. Similarly, plots similar to those of FIG. 4 may be used by control unit 100 to detect an occlusion or kink in drain line 36 downstream of PD fluid pump 70 when pushing used PD fluid to drain.

As discussed above, in one embodiment control unit 100 is programmed to compare a most recently sensed set of maximum and minimum pressure sensor output peaks may be compared to maximum and minimum pressure sensor output peaks sensed just prior to the most recent set. At the beginning of treatment however there is no precedent. So assuming for example that the very first pumping procedure of a treatment is for control unit 100 to cause effluent or used PD fluid to be removed from the patient (e.g., from a previous treatment or a midday exchange), control unit 100 may use high and low sets of upstream (e.g., negative) pressure peaks recorded during a priming procedure performed before the initial patient drain. Control unit 100 here may be programmed to use the last or most recent recorded set of high and low upstream (e.g., negative) pressure peaks or an average of multiple sets of high and low upstream (e.g., negative) pressure peaks recorded during the priming procedure for comparison with the first sensed set of high and low upstream (e.g., negative) pressure peaks of the initial patient drain.

Assuming instead that the very first pumping procedure of a treatment is for control unit 100 to cause a patient fill of fresh, heated PD fluid to be delivered to the patient, control unit 100 instead use sets of downstream (e.g., positive) high and low pressure peaks recorded during the priming procedure performed before the initial patient drain. Control unit 100 may again use the last or most recent recorded set of downstream (e.g., positive) high and low pressure peaks or an average of multiple sets of downstream (e.g., positive) high and low pressure peaks recorded during the priming procedure for comparison with the first sensed set of downstream (e.g., positive) high and low pressure peaks of the initial patient fill.

Figure 5:
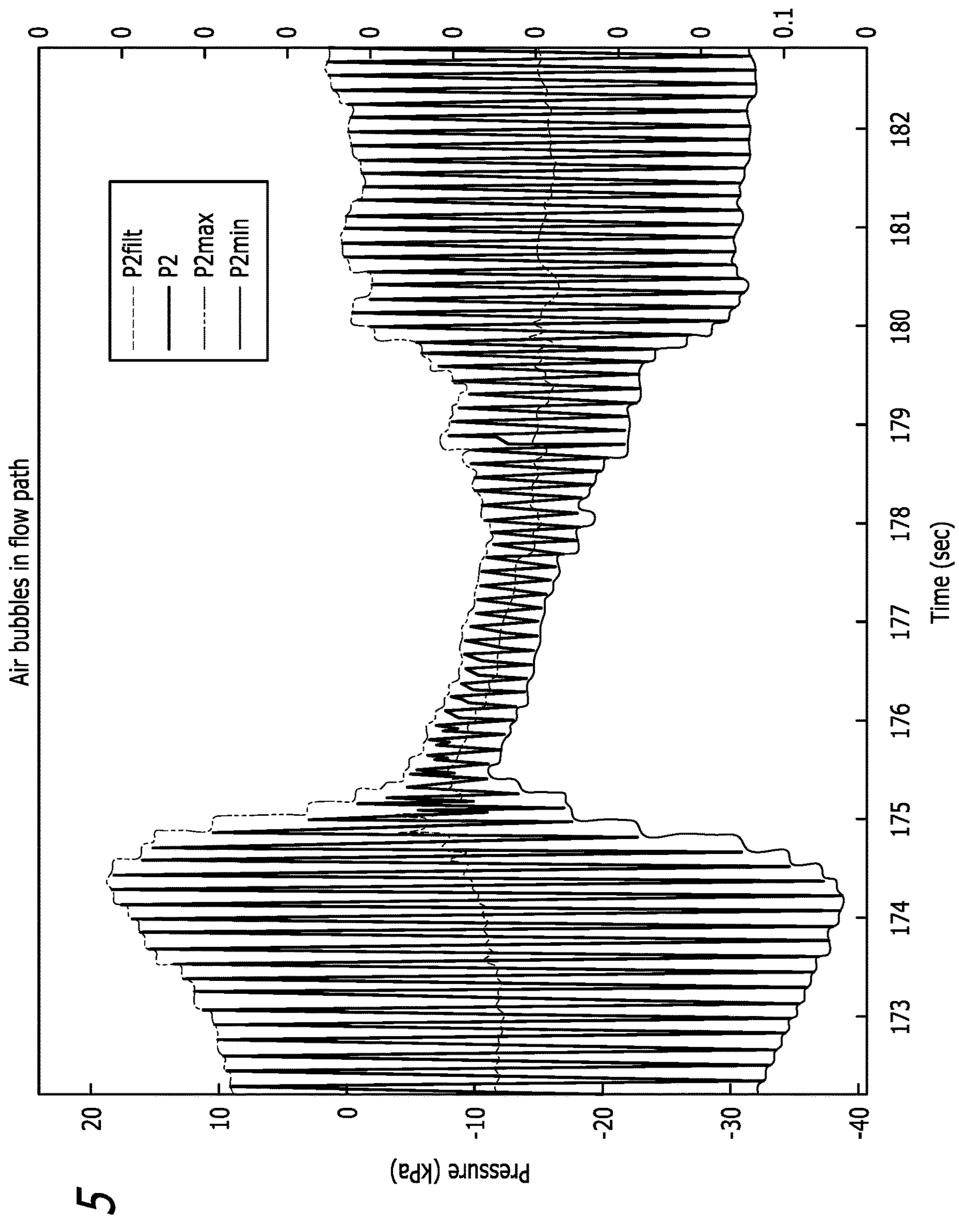
FIG. 5 shows the plots of FIG. 3, wherein each of the plots illustrate a characteristic response to an air bubble in the patient line.
Figure 6:
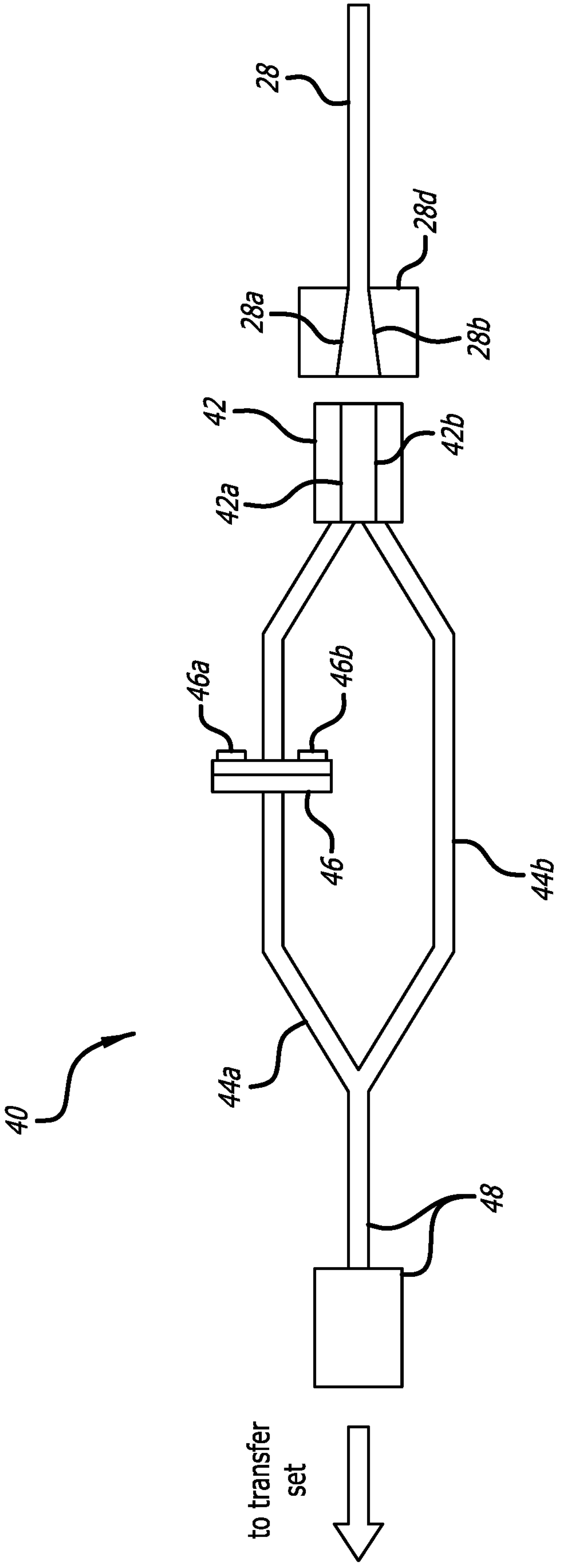
FIG. 6 shows one embodiment of a disposable filter set for connection to a reusable patient line of the present disclosure.

In any of the above embodiments, the control unit 100 is programmed so that air bubbles will not result in a false occlusion detection. FIG. 5 illustrates an example in which an air bubble occurs along the used PD fluid lumen of dual lumen patient line 28. FIG. 5 includes each of the plots described in connection with FIG. 3, including P2filt, P2, P2max, and P2 min. In the presence of air in the patient line, P2 shows that the negative pressure peaks are dampened, such that P2max is decreased and P2 min is increased. Because both the high and low trigger points are not attained, control unit 100 system does not determine that an occlusion has occurred Determining Hydrostatic Pressure at Transfer Set As discussed above, a disposable patient line filter set 40, is connected between reusable patient line 28 and the patient's transfer set. FIG. 6 illustrates disposable patient line filter set 40 in more detail. Disposable patient line filter set 40 may be made, for example, of any of the polymer materials discussed herein. Disposable patient line filter set 40, like reusable patient line 28, is dual line lumen in one embodiment and includes a connector 42 that connects to the distal end of reusable patient line 28. Connector 42 includes a fresh PD fluid lumen 42*a* that communicates with a fresh PD fluid lumen 28*a* of the distal end of reusable patient line 28. Connector 42 also includes a used PD fluid lumen 42*b* that communicates with a used PD fluid lumen 28*b* of the distal end of reusable patient line 28. Disposable patient line filter set 40 also includes (i) a first or fresh disposable line 44*a* that communicates with the fresh PD fluid lumen 28*a* of dual lumen reusable patient line 28 and (ii) a second or effluent disposable line 44*b* that communicates with the used PD fluid lumen 28*b* of dual lumen reusable patient line 28. A final stage or sterilizing grade filter membrane 46 is located in or along first or fresh disposable line 44*a* and provides a final stage of PD fluid filtration prior to delivery to the patient. The sterilizing grade filter member may be positioned at the mid auxiliary line. Sterilizing grade filter membrane 46 is in one embodiment itself sterilized. PD filter membrane 46 can for example be a pass-through filter that does not have a reject line. Pore sizes for sterilizing grade filter membrane 46 may, for example, 0.1 to 0.2 micron. Suitable sterile filters for filter membrane 46 may, for example, be a Pall IV-5 or GVS Speedflow filter membrane, or be a filter membrane provided by the assignee of the present disclosure.

In the illustrated embodiment, the housing of sterilizing grade filter membrane 46 may be provided with one or more hydrophobic filters or vents, e.g., vents 46*a* and 46*b*. In an embodiment, the PD fluid filtering media of sterilizing grade filter membrane 46 is hydrophilic in nature and therefore prevents air from traveling through the filter media once wetted. Sterilizing grade filter membrane 46 accordingly provides a last chance air removal mechanism just prior to the fresh PD fluid reaching the patient. Air collects in the housing of sterilizing grade filter membrane 46 upstream of the filter media, which is vented via hydrophobic filters or vents 46*a* and 46*b* located upstream of the filter medial. Hydrophobic filters or vents 46*a* and 46*b* filter and remove contaminants from any air that might enter the housing of sterilizing grade filter membrane 46 through the vents.

The configuration of disposable patient line filter set 40 allows the patient's intraperitoneal patient pressure ("IPP"), or very close to it, to be measured. Viewing FIG. 6, used PD fluid is removed from left to right through the patient's transfer set, used disposable line 44*b*, used PD fluid lumen 42*b* of disposable connector 42, used PD fluid lumen 28*b* of reusable patient line 28 and into the reusable circuitry inside the cycler 20 under negative pressure. Control unit 100 causes dialysis fluid pump 70 to be run in a reversed drain direction to pull used PD fluid from patient P, through the patient's transfer set, through used disposable line 44*b* of disposable filter set 40, through used PD fluid lumen 28*b* of reusable patient line 28. This results in a negative pressure at the junction between used disposable line 44*b* and fresh disposable line 44*a*. This negative pressure causes a small amount of air to enter through vents 46*a* and 46*b* and collect in the housing of sterilizing grade filter membrane 46 upstream of the filter media. Since the vents 46*a* and 46*b* are open to the atmosphere, the pressure of the air trapped inside the filter housing will equilibrate to atmospheric pressure.

During drain, patient fill valve 54*f* is closed so that patient line 52*f* is closed causing the PD fluid in fresh disposable line 44*a*, fresh PD fluid lumen 42*a*, fresh PD fluid lumen 28*a* and the reusable circuitry inside the cycler 20 (which may still be at least partially fresh PD fluid from the previous patient fill) is static, not moving. Pressure measured by pressure sensor 78*a* as positioned in FIG. 2 will therefore be the atmospheric pressure in the filter plus the hydrostatic pressure due to the difference in height between the filter set 40 and the measuring pressure sensor. The control unit 100 is programmed to store the hydrostatic pressure.

When the PD fluid in used PD fluid lumen 28*b* and the PD fluid in fresh fluid lumen 28*a* are both static and not moving (i.e. flowrate is zero), the pressure measured at pressure sensor 78*b* as positioned in FIG. 2 can be used to calculate IPP. Control unit 100 is programmed to determine when the flow rate in both the used PD fluid lumen 28*b* and the PD fluid in fresh fluid lumen 28*a* are both zero and to determine IPP by subtracting the pressure measured at pressure sensor 78*b* under static conditions with the hydrostatic pressure stored by control unit 100.

Such information may be stored in one or more memory 104 and/or sent from cycler 20 via a wired or wireless connection to a network, e.g., the internet, for storage and analysis in a doctor's or clinician's database.

In one embodiment control unit 100 is programmed to compare a most recently calculated IPP value to IPP values stored in the memory 104 from other treatment sessions. Control unit 100 here may be programmed to issue an alarm if the difference between the recently calculated IPP value and the stored IPP value exceeds a predetermined threshold. The control unit 100 may also be configured to analyze trends in the IPP values over time.

Figure 7:
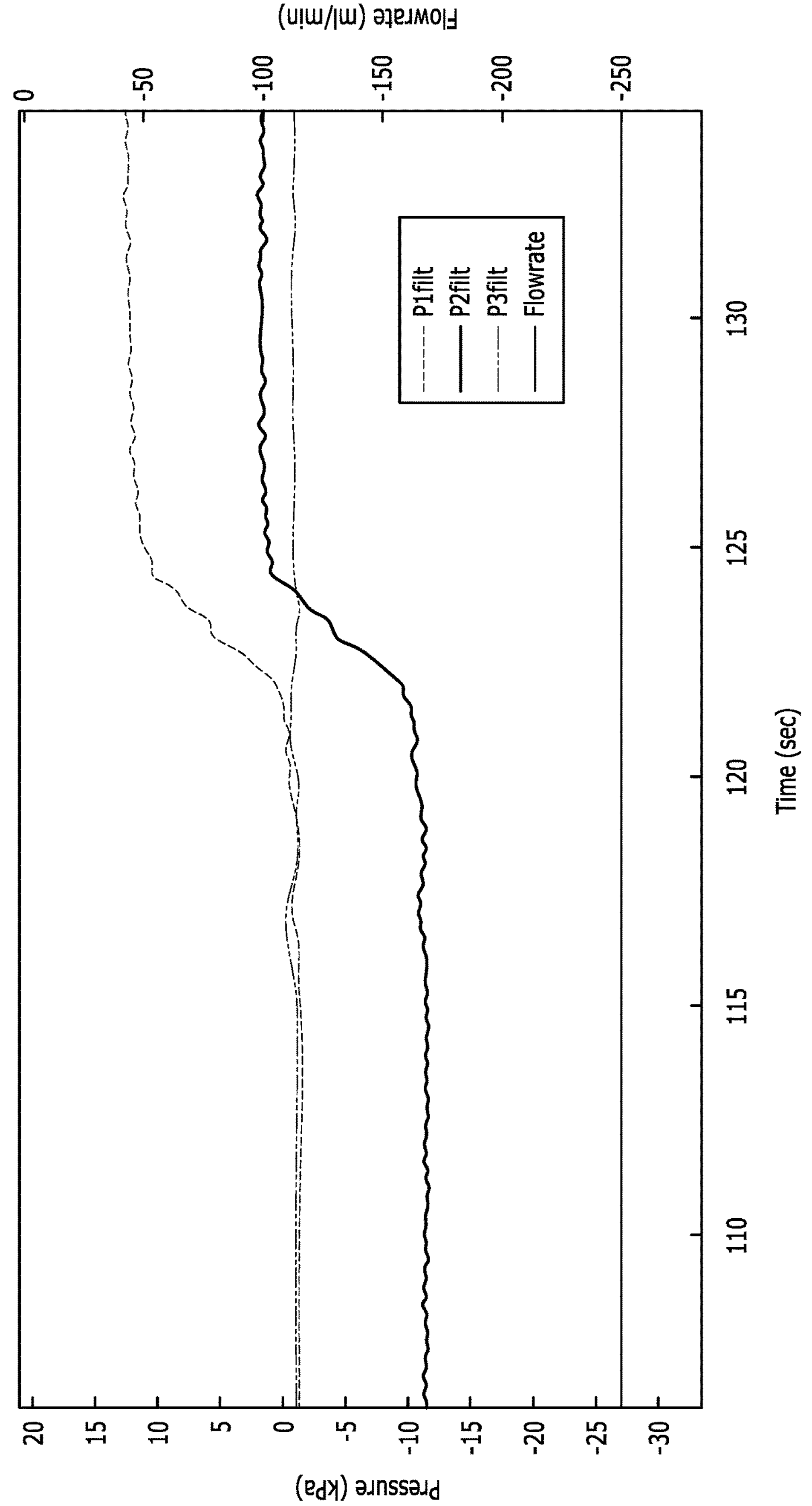
FIG. 7 shows a plot of a filtered negative pressure plot, a positive negative pressure plot, a plot from a test pressure sensor placed at an access point to the patient, and a plot of a corresponding PD flowrate, wherein each of the plots illustrate a characteristic response to moving the simulated peritoneum and disposable set 140 cm above the PD cycler.

FIG. 7 illustrates the output of pressure sensor P1 (78*a*), P2 (sensor 78*b*1, 78*b*2 and/or 78*c*), and P3 as located in FIG. 2 during drain, which has been filtered by control unit 100, e.g., via a high pass filter, low pass filter, or combination band pass filter. FIG. 7 further illustrates that a steady drain flowrate of about 250 milliliters (ml) per minute from patient P into the used PD fluid lumen of dual lumen patient line 28. At the start of the plot, the patient P and the disposable filter set 40 are level (i.e. at the same height) with the pressure sensors of the PD cycler 20. P3 has a slight negative pressure due to a pressure drop in the catheter. As discussed previously, this negative pressure causes a small amount of air to enter through vents 46*a* and 46*b* and collect in the housing of sterilizing grade filter membrane 46 upstream of the filter media. The air acts as damper (i.e. a low pass filter), making the fluid path less stiff.

At 120 seconds, the system 10 is configured so that the patient P and the disposable filter set 40 are 140 cm above the PD cycler 20. As illustrated in FIG. 7, the filtered pressure measurement inside the fresh PD lumen (P1) and the used PD lumen (P2) of patient line 28 increases to about 12 kPa and about 2 kPa, respectively. This is due to a slightly positive pressure in the disposable filter set 40, which causes the trapped air to leave the housing of sterilizing grade filter membrane 46 through vents 46*a* and 46*bm*, which in turn decreases the dampening of the signal.

Figure 8:
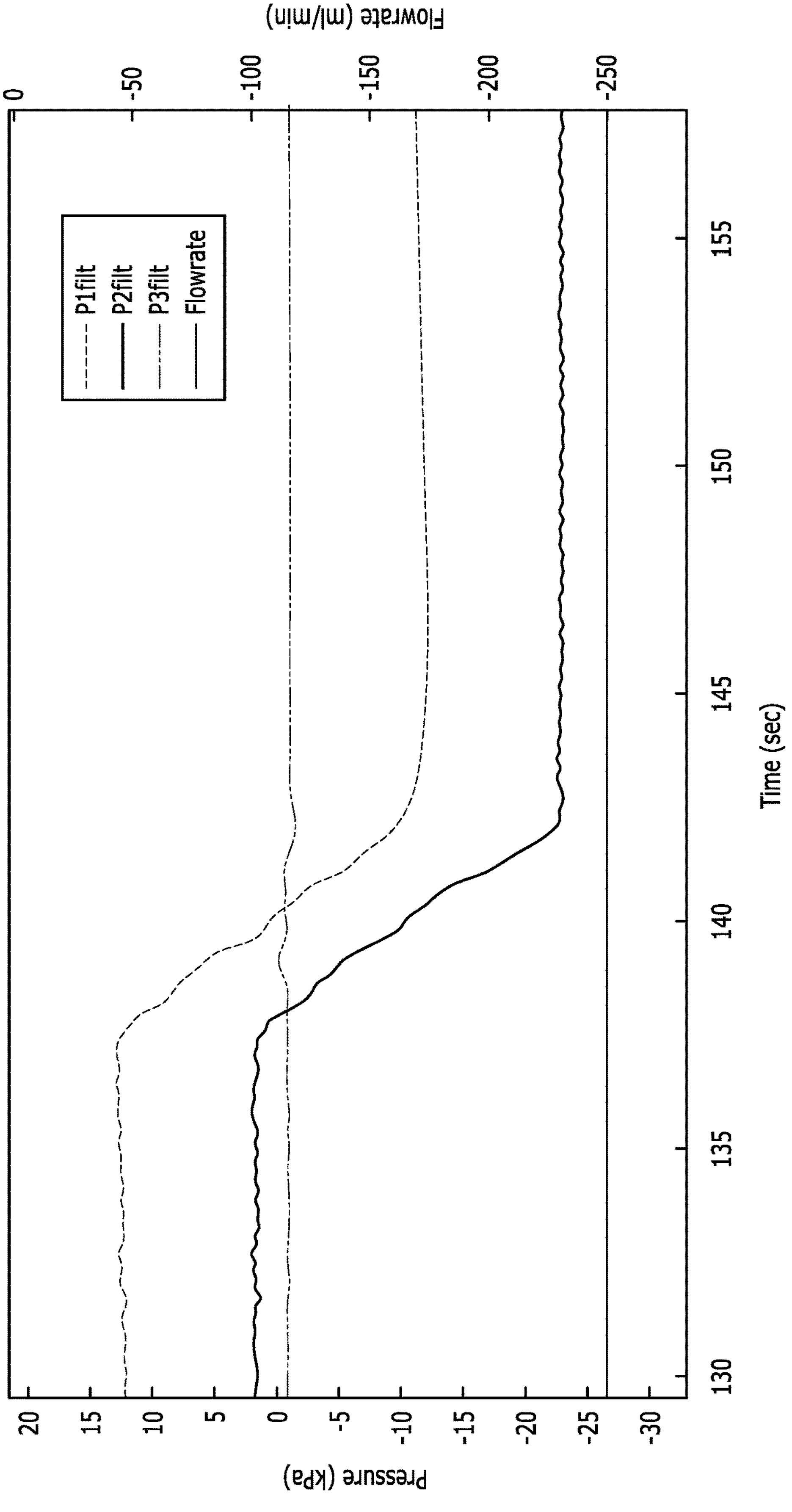
FIG. 8 shows the plot of FIG. 7, wherein each of the plots illustrates a characteristic response to moving the simulated peritoneum and disposable set 120 cm below the PD cycler.

FIG. 8 illustrates the same plot as FIG. 7. At 140 seconds, the system is configured so that the patient P and the disposable filter set 40 are 120 cm below the PD cycler 20. Again, this negative pressure causes a small amount of air to enter through vents 46*a* and 46*b* and collect in the housing of sterilizing grade filter membrane 46 upstream of the filter media. The air acts as damper (i.e. a low pass filter) and makes the fluid path less stiff. In turn, the pressure measurement inside the fresh PD lumen (P1) and the used PD lumen (P2) is decreased to about −12 kPa and about −23 kPa, respectively.

It should be understood that various changes and modifications to the presently preferred embodiments described herein will be apparent to those skilled in the art. It is therefore intended that such changes and modifications be covered by the appended claims. For example, system 10 does not have to use redundant or durable components, does not have to employ disinfection, such as heat disinfection, does not have to employ a dual lumen patient line, and may instead employ a disposable set having a disposable pumping portion that contacts the corresponding medical fluid. Such disposable cassette may employ dual lumen reusable patient line 28, or a single lumen patient line, and may or may not employ disposable filter set 40. Where a single lumen patient line is provided instead, a single one or more pressure sensor may be located along an internal line of PD fluid machine in fluid communication with the single lumen patient line. While disposable filter set 40 would not be needed as a last chance filter for a system not using heat disinfection, disposable filter set 40 may still be provided if the fresh PD fluid is made online at the time of use as a last chance filter for the online PD fluid. PD fluid pumping with the disposable set may be performed alternatively via pneumatic pump actuation of a sheet of a disposable cassette of the disposable set, via electromechanical pump actuation of a sheet of a disposable cassette of the disposable set, or via peristaltic pump actuation of a pumping tube segment provided with the disposable set.

The invention is claimed as follows:

1. A peritoneal dialysis ("PD") system comprising:

a PD fluid pump configured to pump PD fluid along a line under an upstream pressure and to create an upstream pressure profile having a maximum upstream pressure and a minimum upstream pressure;

a pressure sensor positioned and arranged to sense the upstream pressure profile and to produce an output indicative of the upstream pressure profile including a maximum upstream pressure output and a minimum upstream pressure output; and a control unit configured to analyze the output indicative of the upstream pressure profile and to determine that an occlusion in the line has occurred if both the maximum upstream pressure output and the minimum upstream pressure output change by, at, or more than a set pressure delta, wherein the set pressure delta is optionally the same pressure delta for the maximum upstream pressure output and the minimum upstream pressure output.

2. The PD system of claim 1, wherein the set pressure delta is different for the maximum upstream pressure output and the minimum upstream pressure output.

3. The PD system of claim 1, wherein the set pressure delta is selected to avoid a false occlusion detection in the line and so as to detect a partial occlusion in the line.

4. The PD system of claim 1, wherein the upstream pressure profile is a sinusoidal profile.

5. The PD system of claim 1, wherein the line under upstream pressure is a flexible patient line and optionally a used PD fluid lumen of a flexible dual lumen patient line.

6. The PD system of claim 1, wherein the line under upstream pressure is an internal line of a PD machine of the PD system.

7. The PD system of claim 1, wherein the PD fluid pump is located along an internal line in fluid communication with the line under upstream pressure, and wherein the pressure sensor is positioned and arranged along the internal line or a third line in fluid communication with the internal line.

8. The PD system of claim 1, wherein the control unit is configured to determine the change by comparing (i) a most recent maximum upstream pressure output to a next most recent maximum upstream pressure output, and (ii) a most recent minimum upstream pressure output to a next most recent minimum upstream pressure output.

9. The PD system of claim 1, wherein the control unit is configured to determine the change by comparing (i) a most recent maximum upstream pressure output to an average maximum upstream pressure output including a next most recent maximum upstream pressure output, and (ii) a most recent minimum upstream pressure output to an average minimum upstream pressure output including a next most recent minimum upstream pressure output.

10. The PD system of claim 9, wherein at least one of the average maximum upstream pressure output or the average minimum upstream pressure output is a rolling average.

11. The PD system of claim 1, wherein the control unit is configured to determine the change by comparing (i) an average maximum upstream pressure output including a most recent maximum upstream pressure output and at least one other maximum upstream pressure output to (a) a maximum upstream pressure output just prior to the at least one other maximum upstream pressure output or (b) a second average maximum upstream pressure output including the just prior maximum upstream pressure output, and (ii) an average minimum upstream pressure output including a most recent minimum upstream pressure output and at least one other minimum upstream pressure output to (a) a minimum upstream pressure output just prior to the at least one other minimum upstream pressure output or (b) a second average minimum upstream pressure output including the just prior minimum upstream pressure output.

12. The PD system of claim 1, wherein the control unit is configured such that upon determining that an occlusion in the line has occurred, at least one of (i) the PD fluid pump is stopped or (ii) an alarm is sounded and/or displayed.

13. The PD system of claim 1, wherein the upstream pressure is a negative pressure.

14. A peritoneal dialysis ("PD") system comprising:

a PD fluid pump configured to pump PD fluid along a line under pressure and to create a pressure profile having a maximum pressure and a minimum pressure;

a pressure sensor positioned and arranged to sense the pressure profile and to produce an output indicative of the pressure profile including a maximum pressure output and a minimum pressure output; and a control unit configured to analyze the output indicative of the pressure profile and to determine that an occlusion in the line has occurred if both the maximum pressure output and the minimum pressure output change by, at, or more than a set pressure delta, wherein the set pressure delta is optionally the same pressure delta for the maximum pressure output and the minimum pressure output.

15. The PD system of claim 14, wherein the PD fluid pump is configured to pump PD fluid along the line under negative pressure, and wherein the maximum pressure output is a maximum negative pressure output and the minimum pressure output is a minimum negative pressure output.

16. The PD system of claim 15, wherein the line is (i) a patient line, optionally a used PD fluid lumen of a dual lumen patient line or (ii) a PD fluid supply line.

17. The PD system of claim 14, wherein the PD fluid pump is configured to pump PD fluid along the line under positive pressure, and wherein the maximum pressure output is a maximum positive pressure output and the minimum pressure output is a minimum positive pressure output.

* * * * *